United States Patent
Kankan et al.

(10) Patent No.: US 9,890,121 B2
(45) Date of Patent: Feb. 13, 2018

(54) PROCESS FOR PREPARING ATAZANAVIR SULPHATE

(71) Applicant: Cipla Limited, Mumbai (IN)

(72) Inventors: Rajendra Narayanrao Kankan, Mumbai (IN); Srinivas Laxminarayan Pathi, Bangalore (IN); Venugopalarao Chinimilli, Bangalore (IN)

(73) Assignee: Cipla Limited, Mumbai (IN)

( * ) Notice: Subject to any disclaimer, the term of this patent is extended or adjusted under 35 U.S.C. 154(b) by 16 days.

(21) Appl. No.: 14/767,054

(22) PCT Filed: Feb. 12, 2014

(86) PCT No.: PCT/GB2014/050404
§ 371 (c)(1),
(2) Date: Aug. 11, 2015

(87) PCT Pub. No.: WO2014/125270
PCT Pub. Date: Aug. 21, 2014

(65) Prior Publication Data
US 2016/0002166 A1    Jan. 7, 2016

(30) Foreign Application Priority Data
Feb. 12, 2013  (IN) .......................... 423/MUM/2013

(51) Int. Cl.
| | | |
|---|---|---|
| *C07D 211/70* | (2006.01) | |
| *C07D 211/82* | (2006.01) | |
| *C07D 213/06* | (2006.01) | |
| *C07D 213/58* | (2006.01) | |
| *C07D 213/42* | (2006.01) | |

(52) U.S. Cl.
CPC ......... *C07D 213/58* (2013.01); *C07D 213/42* (2013.01)

(58) Field of Classification Search
None
See application file for complete search history.

(56) References Cited

U.S. PATENT DOCUMENTS

| | | | |
|---|---|---|---|
| 5,849,911 A | 12/1998 | Fässler et al. | |
| 6,087,383 A | 7/2000 | Singh et al. | |
| 2013/0035493 A1* | 2/2013 | Kao .................... | C07D 213/42 546/332 |

FOREIGN PATENT DOCUMENTS

| | | |
|---|---|---|
| IN | 423MUM2013 | 2/2013 |
| WO | 9936404 A1 | 7/1999 |
| WO | 2005108349 A2 | 11/2005 |

(Continued)

OTHER PUBLICATIONS

Chang, HR. et al. Atazanavir Urolithiasis. New England Journal of Medicine. 2006, vol. 20, p. 2158.*

(Continued)

*Primary Examiner* — Andrew D Kosar
*Assistant Examiner* — Ben S Michelson
(74) *Attorney, Agent, or Firm* — Conley Rose, P.C.; Rodney B. Carroll

(57) ABSTRACT

The present invention relates to a process for the preparation of Compound (A):

Compound (A)

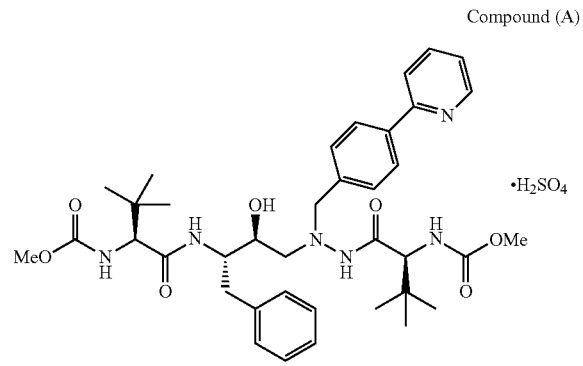

wherein the process comprises contacting atazanavir base (Compound (II))

(II)

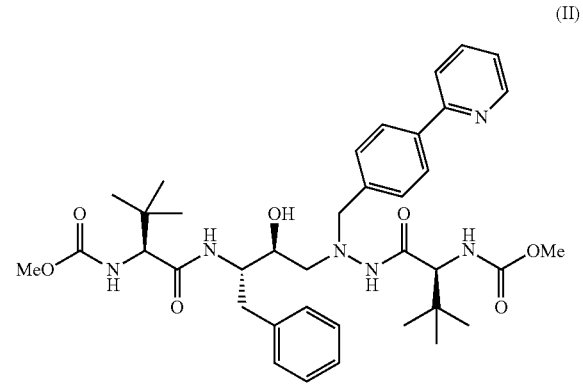

with sulphuric acid in a combination of two or more solvents and isolating compound (A). The present invention also relates to substantially pure Compound (A), and to Compound (A) devoid of mesityl oxide impurity. Mesityl oxide has the following formula:

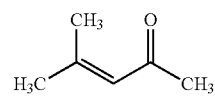

18 Claims, No Drawings

(56) References Cited

FOREIGN PATENT DOCUMENTS

| WO | WO 2005/108349 A2 | * | 11/2005 |
|----|-------------------|---|---------|
| WO | 2010079497 A2 | | 7/2010 |
| WO | 2011027324 A1 | | 3/2011 |
| WO | 2014030173 A2 | | 2/2014 |
| WO | 2014125270 A1 | | 8/2014 |
| WO | 2014125270 A8 | | 8/2014 |

OTHER PUBLICATIONS

Mohrig, Jr. et al. Techniques in Organic Chemistry. Third Ed. 2010, see technique 15.*

Foreign communication from a related counterpart application—International Search Report and Written Opinion, PCT/GB2014/050404, dated Mar. 20, 2014, 14 pages.

Foreign communication from a related counterpart application—International Preliminary Report on Patentability, PCT/GB2014/050404, Aug. 18, 2015, 10 pages.

Foreign communication from a related counterpart application—Third Party Observation, PCT/GB2014/050404, Feb. 18, 2015, 1 page.

Stahl, P. Heinrich, "Preparation of Water-Soluble Compounds Through Salt Formation," The Practice of Medicinal Chemistry, XP-002566271, 2003, pp. 601-615, Elsevier.

Technical Disclosure, "Process for the Preparation of Amorphous Atazanavir Bisulfate," Prior Art Database, Aug. 22, 2007, 5 pages, IP.com.

Xu, Zhongmin, et al., "Process Research and Development for an Efficient Synthesis of teh HIV Protease Inhibitor BMS-232632," Organic Process Research & Development, 2002, pp. 323-328, vol. 6, No. 3, American Chemical Society.

Foreign Communication from a related counterpart application—European Examination Report dated Sep. 9, 2016, in EP Application No. 14705560.2, 6 pages.

Specification of Indian application filed Dec. 5, 2009 and entitled, "Process for Preparing Atazanavir Bisulfate and Novel Forms," retrieved from http://ipindiaonline.gov.in/patentsearch/search/index.aspx, dated Aug. 29, 2016, 8 pages (XP055298147).

* cited by examiner

PROCESS FOR PREPARING ATAZANAVIR SULPHATE

CROSS-REFERENCE TO RELATED APPLICATIONS

This application is a filing under 35 U.S.C. 371 of International Application No. PCT/GB2014/050404 filed Feb. 12, 2014, entitled "Process for Preparing Atazanavir Sulphate" which claims priority to Indian Patent Application No. 423/MUM/2013 filed Feb. 12, 2013, which applications are incorporated by reference herein in their entirety.

TECHNICAL FIELD OF THE INVENTION

The present invention relates to atazanavir sulphate Form A and to a process for preparing atazanavir sulphate Form A.

BACKGROUND OF THE INVENTION

Atazanavir sulfate is known by the chemical name (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioic acid dimethyl ester sulfate. Atazanavir sulfate is an antiviral agent and HIV protease inhibitor.

Atazanavir sulfate is represented by the structural formula I:

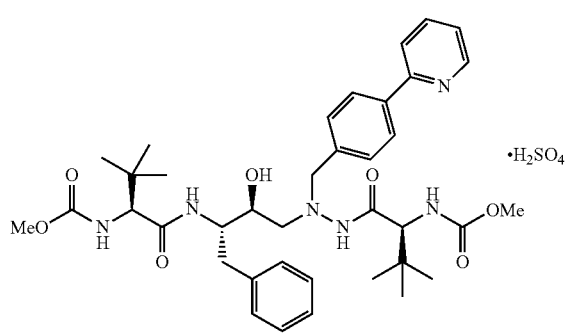

(I)

The free base of atazanavir is represented by the structural formula II:

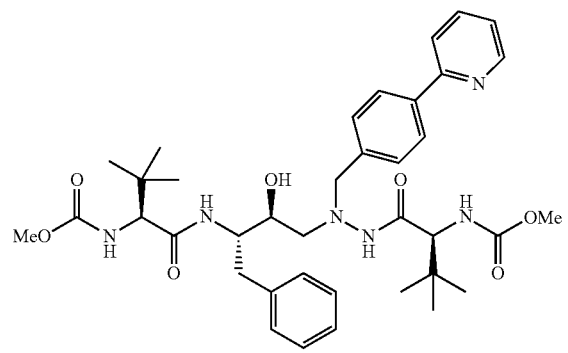

(II)

U.S. Pat. No. 5,849,911 describes a series of azapeptide HIV protease inhibitors including atazanavir. According to U.S. Pat. No. 5,849,911, atazanavir is obtained by either crystallization from ethanol/water, or by precipitation with ether from methylene chloride solution of the compound. U.S. Pat. No. 5,849,911 indicates that atazanavir methane sulfonate is precipitated with ether from a methylene chloride solution of atazanavir methane sulfonate, followed by drying under reduced pressure; whereas atazanavir hydrochloride is precipitated by mixing a dioxane solution of atazanavir with a dioxane solution of hydrochloride.

U.S. Pat. No. 6,087,383 describes the preparation of crystalline atazanavir bisulfate in the form of Type-II crystals, which are hydrated, hygroscopic crystalline form, and Type-I crystals, which are anhydrous/desolvated crystalline form. U.S. Pat. No. 6,087,383 discloses the preparation of Type-I crystals by treating atazanavir sulfate with acetonitrile, ethanol-heptane or acetone. Type-II crystals are obtained from isopropanol crystallization.

WO 2005/108349 discloses two crystal forms, Pattern C and Form E3 of atazanavir bisulfate. WO 2005/108349 also discloses a process for the preparation of atazanavir bisulfate Form A. According to WO 2005/108349, Pattern C crystals of atazanavir bisulfate are obtained by stirring a suspension of the Form A crystals of atazanavir bisulfate in water.

Organic Process Research and Development, 6, p. 323-328 (2002) describes the preparation of Type-I crystals of atazanavir sulfate from ethanol crystallization. Organic Process Research and Development, 12, p. 69-75 (2008) discloses crystallization of atazanavir free base with an ethanol-water solvent system.

WO 2010/079497 discloses the crystalline Form H1 of atazanavir sulphate and also a process for the preparation of the same. According to WO 2005/108349, atazanavir sulfate is dissolved in methanol, then ethyl acetate is added, and the solid obtained is collected by filtration and dried to give atazanavir sulfate in crystalline Form H1.

WO 2011/027324 discloses the polymorphic Forms B and P of atazanavir sulfate and processes for their preparation. According to WO 2011/027324, the process for preparing crystalline polymorphic Form B of atazanavir sulfate comprises dissolving atazanavir sulphate in n-butanol and evaporating the solvent at 45-55° C. According to WO 2011/027324, the process for preparing crystalline polymorphic Form P comprises dissolving atazanavir sulfate in n-propanol and evaporating the solvent under vacuum at 35-45° C.

Atazanavir sulphate shows the phenomenon of polymorphism. It is apparent from the prior art that the same solvent can give different polymorphs under different experimental conditions. It has been demonstrated that the known commercial process for preparing crystalline atazanavir sulphate produces, exclusively, a highly crystalline form, Form A, and this is considered as the most suitable polymorph for formulation of atazanavir sulphate. Only very few solvent systems, such as acetone, or acetonitrile, may be used to obtain Form A. However, it is indicated in U.S. Pat. No. '383 and WO '349 that if these solvents are used, the resulting Form A contains impurities, and the most probable impurity is mesityl oxide impurity, which is genotoxic. In order to remove this impurity, atazanavir sulphate must be exposed to repeated washing and drying procedures.

Hence, a person skilled in the art, when synthesizing Form A, would consider the use of solvent systems other than acetone or any other aliphatic ketones, so as to avoid formation of impurities, desirable. However, it has been found that when a solvent medium other than acetone, ethanol/n-heptane system, or acetonitrile is used, Form A is not obtained.

There is a clear need for a process that overcomes the difficulties encountered in the prior art processes for preparing Form A. In particular, there is a need for an alternate process for preparing Form A that can effectively control the generation of potential impurities. The present invention seeks to address these issues.

SUMMARY OF THE INVENTION

The present invention provides a process for preparing atazanavir sulphate Form A from atazanavir base. The atazanavir sulphate Form A prepared by the process of the invention is substantially free of impurities. Thus, the present invention also provides substantially pure atazanavir sulphate Form A.

"Substantially pure atazanavir sulphate Form A" may be defined as atazanavir sulphate Form A having about 0.3% by weight of total impurities or less, preferably about 0.2% by weight of total impurities or less, more preferably about 0.1% by weight of total impurities or less. Substantially pure atazanavir sulphate Form A prepared according to the present invention is also, advantageously, devoid of mesityl oxide impurity. Mesityl oxide has the following formula:

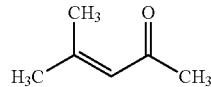

"Devoid of mesityl oxide impurity" is defined herein to mean that mesityl oxide impurity is not detectable in the product when the product is analysed using HPLC with a detection limit of 3.75 ppm.

Atazanavir sulphate Form A is referred to hereinafter as "Compound (A)".

According an aspect of the invention there is provided a process for the preparation of substantially pure Compound (A), comprising: contacting atazanavir base (Compound (II))

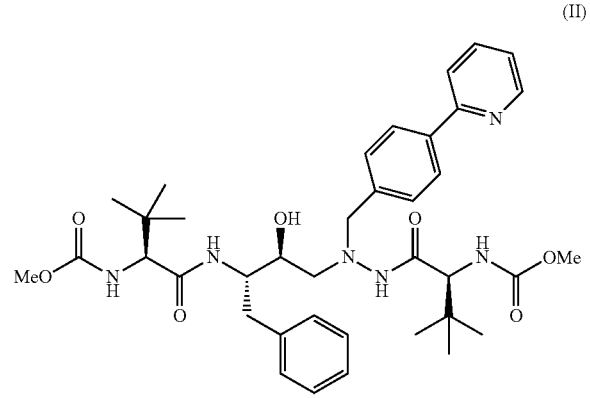 [SMILES: COC(=O)N[C@H](C(=O)N[C@@H](Cc1ccccc1)[C@@H](O)CN(Cc1ccc(-c2ccccn2)cc1)NC(=O)[C@@H](NC(=O)OC)C(C)(C)C)C(C)(C)C]

with sulphuric acid in a combination of two or more solvents and isolating Compound (A).

According to another aspect of the invention there is provided a process for the preparation of Compound (A):

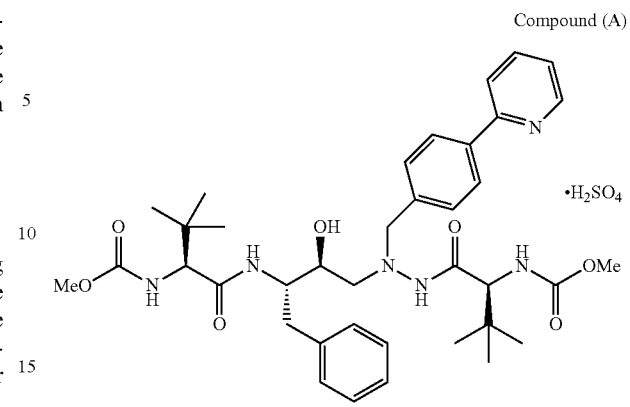

wherein the process comprises contacting atazanavir base (Compound (II))

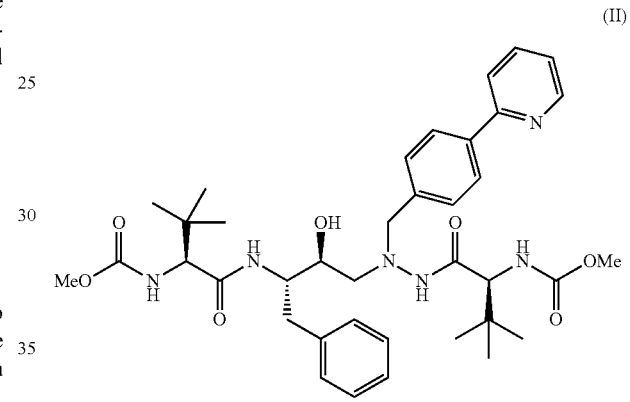

with sulphuric acid in a combination of two or more solvents and isolating Compound (A).

The combination of two or more solvents may comprise a first solvent that is a water immiscible, or moderately soluble in water, solvent, and a second solvent that is a water miscible solvent.

The combination of two or more solvents may comprise a water miscible solvent that is a polar protic solvent or a polar aprotic solvent.

The combination of two or more solvents may comprise a first solvent that is a water immiscible, or moderately soluble in water, solvent and a second solvent that is a water miscible and polar aprotic or polar protic solvent.

The combination of two or more solvents may comprise a water immiscible, or moderately soluble in water, solvent that is selected from the group consisting of: esters, ethers and hydrocarbons.

The combination of two or more solvents comprises a water immiscible, or moderately soluble in water, solvent that is selected from the group consisting of: ethyl acetate, isopropyl acetate, and isobutyl acetate.

The combination of two or more solvents may comprise a water miscible solvent selected from the group consisting of: alcohol, dimethylsulfoxide, and dimethylformamide.

The combination of two or more solvents may comprise two solvents. The combination of two solvents may comprise a first solvent that is a water immiscible, or moderately soluble in water, solvent, and a second solvent that is a water miscible solvent, and the ratio of first solvent to second solvent may be in the range of 10:3 to 10:1. The ratio of first solvent to second solvent may be 10:3, 10:2 or 10:1, and is preferably 10:1.

Alternatively, the combination of two or more solvents may comprise more than two solvents.

The combination of solvents may be selected from the following group:
a) ethyl acetate-methanol;
b) ethylacetate-dimethylsulfoxide;
b) ethyl acetate-dimethylformamide;
c) isopropyl acetate-methanol;
d) isopropyl acetate-dimethylsulfoxide; and
e) isopropyl acetate-dimethylformamide.

The combination of solvents may be ethyl acetate-methanol.

The sulphuric acid used in the process of the invention may be a neat sulphuric acid. The sulphuric acid may be added at a temperature ranging from about 35° C. to about 60° C., and is preferably added at a temperature of about 43±2° C.

Compound (A) may be isolated by filtration. Compound (A) may precipitate prior to isolation, and the precipitated solid may be mixed with a water immiscible solvent, which may be ethyl acetate.

According to another aspect of the invention there is provided Compound (A), wherein Compound (A) is substantially pure Compound (A):

Compound (A)

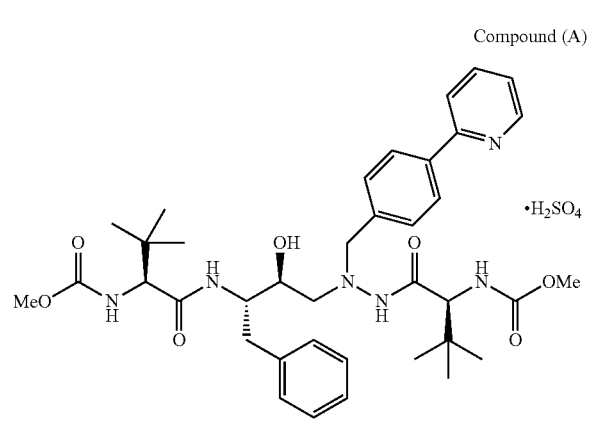

According to another aspect of the invention there is provided Compound (A), wherein Compound (A) is devoid of mesityl oxide impurity:

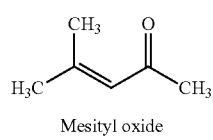

Mesityl oxide

Preferably Compound (A) is substantially pure and devoid of mesityl oxide impurity.

Preferably Compound (A) has about 0.2% by weight of total impurities or less, more preferably about 0.1% by weight of total impurities or less.

Preferably Compound (A) is prepared by a process as defined above.

Preferably Compound (A) is obtainable by a process as defined above.

According to another aspect of the invention there is provided a process for the preparation of Compound (A):

Compound (A)

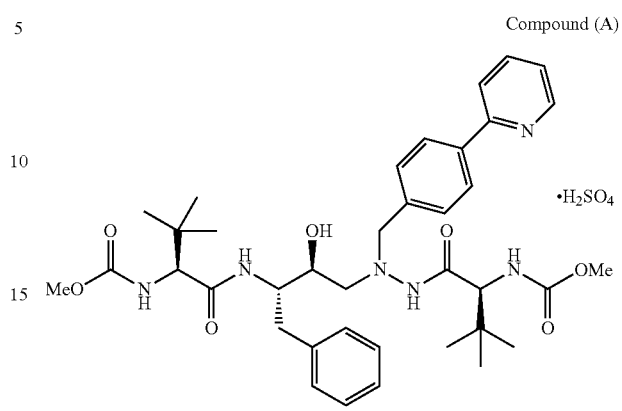

wherein the process comprises contacting atazanavir base (Compound (II))

(II)

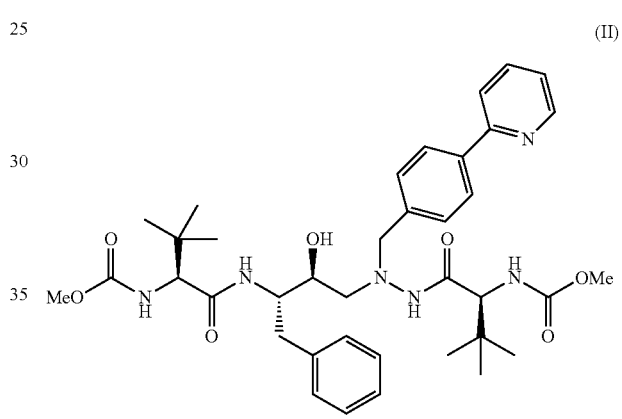

with sulphuric acid in a combination of two or more solvents and isolating Compound (A), wherein the combination of solvents results in the formation of substantially pure Compound (A).

According to another aspect of the invention there is provided a process for the preparation of Compound (A):

Compound (A)

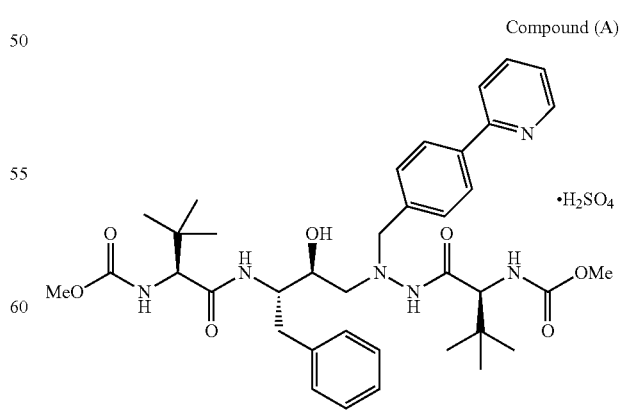

wherein the process comprises contacting atazanavir base (Compound (II))

(II)

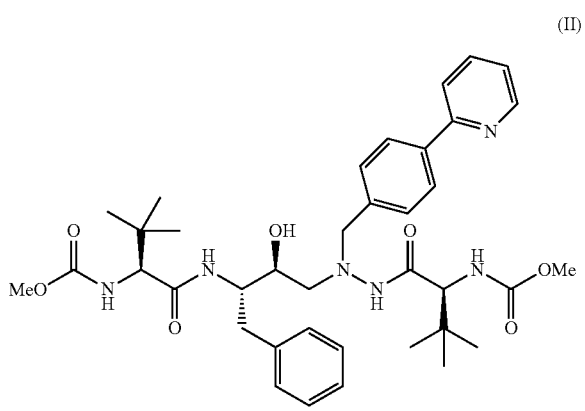 [SMILES: COC(=O)N[C@H](C(=O)N[C@@H](Cc1ccccc1)[C@@H](O)CN(Cc1ccc(-c2ccccn2)cc1)NC(=O)[C@@H](NC(=O)OC)C(C)(C)C)C(C)(C)C]

with sulphuric acid in a combination of two or more solvents and isolating Compound (A), wherein the combination of solvents results in the formation of Compound (A) devoid of mesityl oxide impurity:

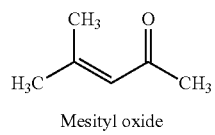

Mesityl oxide

Preferably the combination of solvents results in the formation of Compound (A) that is substantially pure and devoid of mesityl oxide impurity.

In the following aspects of the invention, the substantially pure Compound (A) is preferably prepared by the process as described herein.

In a further aspect of the invention there is provided a pharmaceutical composition comprising substantially pure Compound (A), together with one or more pharmaceutically acceptable excipients. The pharmaceutical compositions of the invention may be prepared according to methods known in the art. The suitable pharmaceutically acceptable excipients for inclusion in such pharmaceutical compositions would be known to those skilled in the art.

The substantially pure Compound (A) may be present in the pharmaceutical composition in combination with another active pharmaceutical ingredient. Suitable active pharmaceutical ingredients for combination with substantially pure Compound (A) would be known to those of skill in the art.

In a further aspect of the invention there is provided substantially pure Compound (A) for use in medical treatment.

In a further aspect of the invention there is provided substantially pure Compound (A) for use as an HIV protease inhibitor in a patient in need thereof.

In a further aspect of the invention there is provided substantially pure Compound (A) for use as an anti-viral agent in a patient in need thereof.

In a further aspect of the invention there is provided the use of substantially pure Compound (A) in the manufacture of a medicament for use in inhibiting HIV protease in a patient in need thereof.

In a further aspect of the invention there is provided the use of substantially pure Compound (A) in the manufacture of a medicament for use in treating diseases caused by retroviruses, particularly acquired immune deficiency syndrome or its preliminary stages or an HIV infection, in a patient in need thereof.

In a further aspect of the invention there is provided a method of treating a retroviral disease in a patient in need thereof comprising administering substantially pure Compound (A) to the patient.

In a further aspect of the invention there is provided a method of treating acquired immune deficiency syndrome or its preliminary stages or an HIV infection in a patient in need thereof comprising administering substantially pure Compound (A) to the patient.

According to another aspect of the invention there is provided a process of removing mesityl oxide impurity from Compound (A), wherein the process comprises (i) preparing atazanavir sulphate by methods described in the prior art which are herein incorporated by reference in their entirety and slurrying atazanavir sulphate in a combination of solvents and (ii) isolating Compound (A). Preferably the combination of solvents used in step (i) is as defined above according to the previous aspects of the invention. The Compound (A) that is isolated in step (ii) of this process may be substantially pure and may be devoid of mesityl oxide impurity.

DETAILED DESCRIPTION OF THE INVENTION

The present inventors have developed a process for preparing atazanavir sulphate, more specifically, Form A of atazanavir sulphate [hereinafter referred to as "Compound (A)"]. The process of the invention not only results in the formation of pure Compound (A), but also the product is devoid of mesityl oxide impurities. As used herein, the term "substantially free" refers to atazanavir sulphate Form A having about 0.3% by weight of total impurities or less, preferably about 0.2% by weight of total impurities or less, more preferably about 0.1% by weight of total impurities or less. The total impurity contents described herein relates to the impurities related to atazanavir sulphate as determined by high performance liquid chromatography (HPLC).

According to an aspect of the present invention, there is provided a process for the preparation of Compound (A) that comprises preparing atazanavir sulphate by treating atazanavir base (Compound (II)) with sulphuric acid in a combination of solvents, and isolating Compound (A).

Preferably, according to the present invention, a combination of solvents is used, in place of the aliphatic ketones used in the prior art, such as acetone, to obtain Compound (A). Compound (A) prepared by the process of the invention is, at least substantially, free of impurities.

The process of the present invention may be particularly advantageous in that the need for repeated processing, such as washing and drying of Compound (A) to remove genotoxic impurity mesityl oxide, may be avoided.

Preferred experimental conditions for the process for preparing Compound (A) are depicted in scheme I:

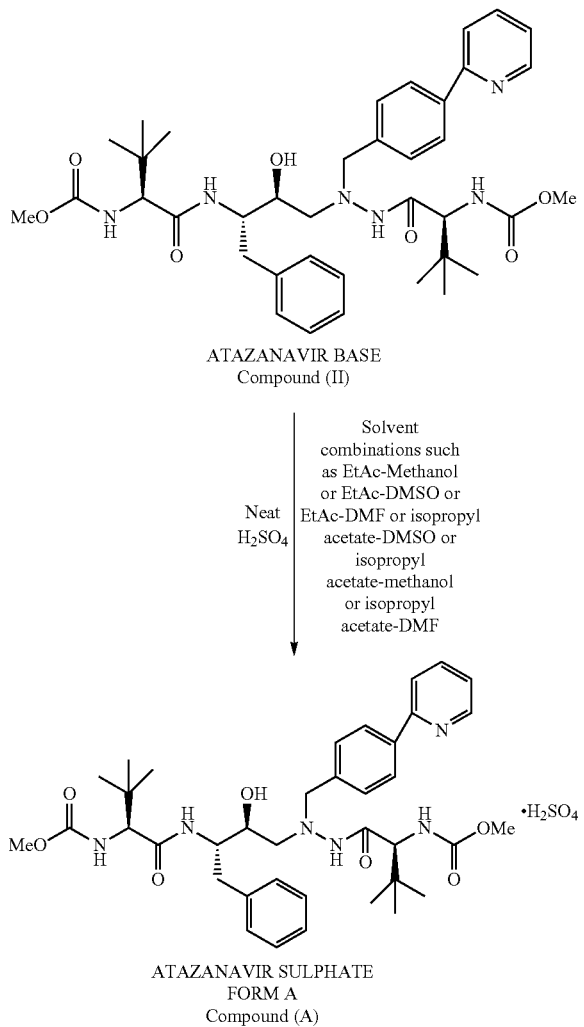 [SMILES: COC(=O)N[C@H](C(=O)N[C@@H](Cc1ccccc1)[C@@H](O)CN(Cc1ccc(-c2ccccn2)cc1)NC(=O)[C@@H](NC(=O)OC)C(C)(C)C)C(C)(C)C ; "H2SO4" ; COC(=O)N[C@H](C(=O)N[C@@H](Cc1ccccc1)[C@@H](O)CN(Cc1ccc(-c2ccccn2)cc1)NC(=O)[C@@H](NC(=O)OC)C(C)(C)C)C(C)(C)C ; "·H2SO4"]

The present invention preferably provides a process for preparing Compound (A) comprising treating Compound (II) with sulphuric acid in the presence of a combination of solvents and isolating Compound (A).

The purity (measured by HPLC) of the Compound (A) obtained according to the present invention is preferably above 99.6%, more preferably above 99.7%, more preferably above 99.8%, and still more preferably 99.9% or more.

Compound (II) used as a starting material may be prepared by the processes known in the art, for example by using (1-[4-(pyridin-2-yl)phenyl]-5(S)-2,5-bis[tert-butoxycarbonyl)amino]-4(S)-hydroxy-6-phenyl-2-azahexane [Di-BOC compound] as the precursor.

The sulphuric acid may be a concentrated sulphuric acid, and preferably a neat sulphuric acid is used. A neat sulphuric acid is defined herein as 98% pure sulphuric acid. Neat sulphuric acid is available commercially.

The addition of sulphuric acid may be carried out at elevated temperature, and is preferably carried out at a temperature ranging from about 35° C. to about 60° C., more preferably ranging from about 40° C. to about 55° C., most preferably about 43±2° C.

The combination of solvents used in the process of the present invention may comprise a combination of two or more water miscible solvents, a combination of two or more water immiscible, or moderately soluble in water, solvents, or a combination of one or more water miscible solvents and one or more water immiscible, or moderately soluble in water, solvents.

The combination of solvents may comprise one or more water immiscible, or moderately soluble in water, solvents selected from the group consisting of esters, hydrocarbons, and ethers. Preferably the combination of solvents comprises an ester such as ethyl acetate, isopropyl acetate, or isobutyl acetate.

The combination of solvents may comprise one or more water miscible solvents selected from the group consisting of polar protic solvents and polar aprotic solvents. Preferably the combination of solvents comprises one or more solvents selected from the group consisting of alcohol, dimethyl formamide (DMF), and dimethyl sulphoxide (DMSO).

Preferably the combination of solvents comprises a water immiscible, or moderately soluble in water, solvent, and a water miscible solvent. Preferably the combination of solvents comprises a polar solvent and a non-polar, or weakly polar, or borderline polar aprotic, solvent. The polar solvent may be protic or aprotic. More preferably the combination of solvents comprises a first solvent that is water immiscible, or moderately soluble in water, and non-polar, or weakly polar, or borderline polar aprotic, and a second solvent that is water miscible and polar protic or polar aprotic.

The combination of solvents may comprise a first solvent that is water immiscible and borderline polar aprotic and a second solvent that is water miscible and polar protic.

The combination of solvents may comprise a first solvent that is water immiscible and borderline polar aprotic and a second solvent that is water miscible and polar aprotic.

The combination of solvents may comprise a first solvent that is moderately soluble in water and non-polar to weakly polar and a second solvent that is water miscible and polar aprotic.

Preferably the combination of solvents comprises two solvents. Alternatively, the combination of solvents may comprise more than two solvents.

Preferably the combination of solvents is selected from the following group of solvent combinations: i) ethyl acetate-methanol, ii) ethyl acetate-dimethyl sulfoxide, iii) ethyl acetate-dimethylformamide, iv) isopropyl acetate-methanol, v) isopropyl acetate-dimethylsulfoxide or vi) isopropyl acetate-dimethylformamide. The most preferable combination of solvents is ethyl acetate-methanol.

The combination of solvents may be prepared by mixing two solvents, preferably one water immiscible, or moderately soluble in water, solvent and one water miscible solvent, in a fixed proportion. The ratio of water immiscible, or moderately soluble in water, solvent to water miscible solvent used in the combination may be in the range of from 10:3 to 10:1. Preferably the ratio is 10:3, 10:2 or 10:1. Most preferably the ratio of solvents used in the combination is 10:1.

According to the process of the present invention, a solid may be obtained when Compound (II) is treated with neat sulphuric acid and a combination of solvents, and the solid is then further isolated to obtain substantially pure Compound (A).

The Compound (A) may be isolated by filtering the solid, washing with a solvent and drying. Preferably the drying is done at a temperature in the range of from about 40° C. to about 65° C., more preferably in the range of from about 50° C. to about 60° C. Most preferably the Compound (A) is dried at about 53±2° C.

The isolation may be, optionally, carried out by mixing the solid with a water immiscible solvent. Preferably, the solid is mixed with a water immiscible solvent selected from the group consisting of esters, hydrocarbons, and ethers. More preferably, the solvent used is ethyl acetate.

An entire preferred process for synthesizing Atzanavir sulphate according to the present invention may be depicted by the following Scheme 2:

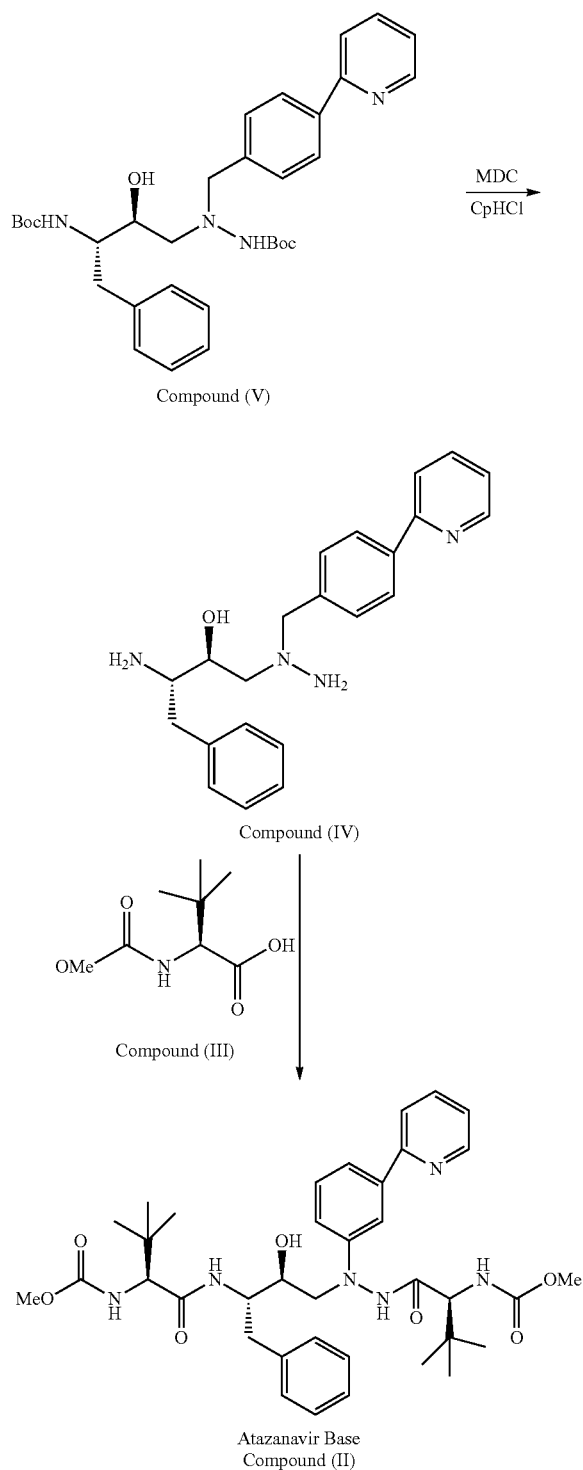

As depicted in Scheme 2, Compound (A) may be prepared using (1-[4-(pyridin-2-yl)phenyl]-5(S)-2,5-bis[tert-butoxycarbonyl)amino]-4(S)-hydroxy-6-phenyl-2-azahexane (Compound (V)) as a starting material. Compound (V) may deprotected using Cp grade HCl in methylene dichloride (MDC) to give (1-[4-(pyridine-2-yl)phenyl]-5(S)-2,5-Diamino]-4(S)-hydroxy-6-phenyl-2-azahexane (Compound (IV)). Compound (IV) may then be reacted with N-methoxy carbonyl-L-tert. leucine to give the atazanavir base (Compound (II)). Compound (II) is then contacted with a combination of solvents, such as EtAc-methanol, or EtAc-DMSO, or ETAc-DMF, or isopropyl acetate-DMSO, or isopropyl acetate-methanol, or isopropyl acetate-DMF, in sulphuric acid to provide atazanavir sulphate (Compound (A)).

The process of the present invention described herein provides Compound (A), which is substantially free of impurities, and in particular, devoid of the gentotoxic impurity mesityl oxide. The level of mesityl impurity is controlled effectively by the process of the present invention as is indicated by non-detection by HPLC of the impurity in Compound (A).

The present invention further provides a Compound (A) devoid of genotoxic impurities, substantially as described hereinbefore, for use in the manufacture of a medicament for the treatment of a viral disease such as HIV-AIDS and/or for the treatment of HIV-AIDS in its preliminary stages.

The present invention further provides a pharmaceutical composition comprising substantially pure atazanavir sulphate Form A (Compound (A)), and a pharmaceutically acceptable carrier.

According to another aspect of the invention there is provided a process of removing mesityl oxide impurity from Compound (A), wherein the process comprises (i) preparing atazanavir sulphate by methods described in the prior art which are herein incorporated by reference in their entirety and slurrying atazanavir sulphate in a combination of solvents and (ii) isolating Compound (A). Preferably the combination of solvents used in step (i) is as defined above according to the previous aspects of the invention. The Compound (A) that is isolated in step (ii) of this process may be substantially pure and may be devoid of mesityl oxide impurity.

While the present invention has been described in terms of its specific embodiments, certain modifications and equivalents will be apparent to those skilled in the art and are intended to be included within the scope of the present invention.

EXAMPLES

Example 1: Preparation of Compound (A) Using Acetone as Per Example 1 of WO 99/36404/U.S. Pat. No. 6,087,383

644 ml of acetone and 92.0 gm of (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioic acid dimethyl ester [Compound (II)] were mixed at 27±2° C. The reaction mass was heated to 50±2° C. 5 M Sulphuric acid (26 ml) was added at 50±2° C. and stirred for an hour. The contents were cooled to 28±2° C., chilled to 3±2° C. and maintained at 3±2° C. for 2 hours. The solid was filtered and washed with 1 volume of heptane. The solid was washed with 80 ml of acetone and dried under vacuum at 53±2° C. for 8 hours. The material was powdered and dried for further 4 hours under vacuum at 53±2° C. The drying process was continued till the LOD (loss on drying) was less than 0.5% w/w to obtain the title compound.

Dry weight: 90-92 gms
Yield: 85.8% to 87.8%
HPLC Purity: 99.6%

Example 2: Preparation of Compound (A) Using Ethyl Acetate:Methanol

A solvent mixture of 500 ml of ethyl acetate and 50 ml of methanol was added to 100 gms of (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioic acid dimethyl ester [Compound (II)]. The reaction mixture was stirred at a temperature of 27±2° C. to get a suspension. The temperature of the suspension was then raised to 43±2° C. and 7.5 ml (13.9 gms) of sulphuric acid was added slowly. The solution was maintained for an hour at a temperature of 43±2° C. whereby a solid was obtained. The material was cooled down to a temperature of 27±2° C. To this 200 ml of ethyl acetate was added, followed by chilling the reaction mixture at a temperature of 3±2° C. The solid obtained was filtered and washed with 1 volume of ethyl acetate. The solid was then exposed to drying process under vacuum at 27±2° C. for 2 hours. The material was powdered and again exposed to drying process under vacuum (630±20 mm of Hg) at 53±2° C. for 4 hours. The drying process was continued till the LOD (loss on drying) was less than 0.5% w/w to obtain the title compound.

Dry weight: 100 gms
Yield: 87.8%
HPLC Purity: 99.9%

Example 3: Preparation of Compound (A)

1) 644 ml of acetone and 92.0 gm of (3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioic acid dimethyl ester [Compound (II)] were mixed at 27±2° C. The reaction mass was heated to 50±2° C. Sulphuric acid (26 ml) was added at 50±2° C. and stirred for an hour. The contents were cooled to 28±2° C., chilled to 3±2° C. and maintained at 3±2° C. for 2 hours, filtered and suck dried.

2) To the solid obtained in step 1), 200 ml of a mixture of ethyl acetate:methanol (10:1) was added, followed by chilling the reaction mixture at a temperature of 3±2° C. The compound obtained was filtered and washed with 1 volume of ethyl acetate. The solid was then exposed to drying process under vacuum at 27±2° C. for 2 hours. The material was powdered and again exposed to drying process under vacuum (630±20 mm of Hg) at 53±2° C. for 4 hours. The drying process was continued till the LOD (loss on drying) was less than 0.5% w/w to obtain the title compound.

Dry weight: 92 gms
Yield: 80.7%

Determination of the Content of Mesityl Oxide Impurity

Method of Analysis

The title compound obtained from the three examples as above was analyzed by HPLC for the content of mesityl oxide.

HPLC Specifications

Column: Purosphere star RP-18e, 10 cm×4.6 mm, 3 µm
Eluent: Gradient of Trifluoro acetic acid buffer and Acetonitrile
Flow: 1.0 ml per minute
Detector: UV
Sample volume: 20 µl
Diluent A: Mix 25 ml ammonia solution (25%) in 475 ml of methanol
Diluent B: Diluent A:water (80:20)
Mobile phase composition and flow rate may be varied in order to achieve required system suitability.

Sample Preparation:

About 500 mg of atazanavir sulphate is weighed in a 10 ml volumetric flask. The sample is dissolved and diluted to volume with diluent B. Sonicated and filtered through 0.45 µm filter.

Standard Preparation:

About 100 mg of mesityl oxide is weighed in a 100 ml volumetric flask. The sample is dissolved and diluted to volume with diluent A. Diluted 10 ml of the solution to 100 ml with diluent A. 5 ml of the above solution transferred to 100 ml volumetric flask and diluted to volume with diluent B.

Method

The freshly prepared sample solutions are injected into the chromatograph and the chromatogram of the sample is continued up to the end of the gradient. The areas for each peak in each solution is determined using a suitable integrator.

Results

The title compound obtained from the three examples as above was analyzed by HPLC for the content of mesityl oxide as shown in Table 1 in accordance with the above method. The results indicate the absence of mesityl oxide impurity by the process of the present invention.

TABLE 1

|  | Mesityl oxide content value |
| --- | --- |
| Example 1 | 13 ppm |
| Example 2 | Not detected |
| Example 3 | Not detected |

The present invention has been described above purely by way of example. It should be noted that modifications in detail may be made within the scope of the appended claims.

The invention claimed is:
1. A process for the preparation of Compound (A):

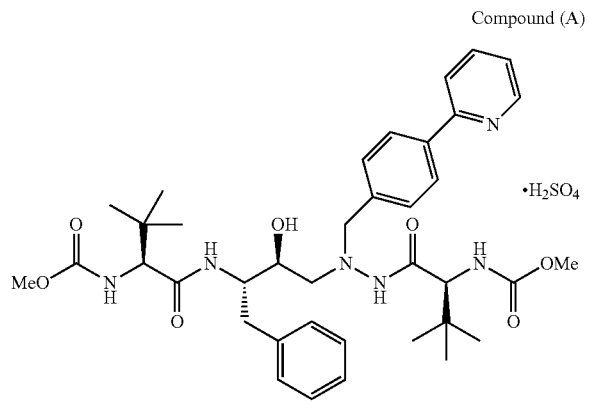

Compound (A)

·H$_2$SO$_4$ wherein the process comprises i) suspending atazanavir base (Compound (II))

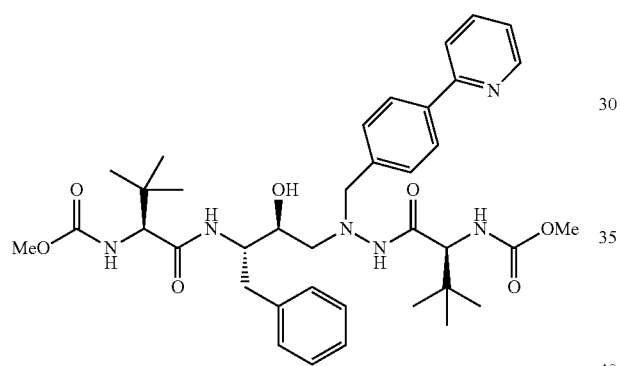

(II)

in a combination of two or more solvents, ii) contacting the suspension of Compound (II) and two or more solvents with sulphuric acid, and iii) isolating Compound (A) wherein the combination of two or more solvents comprises a first solvent which comprises a water immiscible, or moderately soluble in water, solvent that is selected from the group consisting of: ethyl acetate, isopropyl acetate, and isobutyl acetate, and a second solvent which comprises a water miscible solvent that is selected from the group consisting of: alcohol, dimethylsulfoxide, and dimethylformamide and wherein the ratio of first solvent to second solvent is in the range of 10:3 to 10:1.

2. The process according to claim 1, wherein to second solvent is 10:1.

3. The process according to claim 1, wherein the combination of two or more solvents comprises more than two solvents.

4. The process according to claim 1, wherein the combination of solvents is selected from the following group:
   a) ethyl acetate-methanol;
   b) ethyl acetate-dimethylsulfoxide;
   c) ethyl acetate-dimethylformamide;
   d) isopropyl acetate-methanol;
   e) isopropyl acetate-dimethylsulfoxide; and
   f) isopropyl acetate-dimethylformamide.

5. The process according to claim 4, wherein the combination of solvents is ethyl acetate-methanol.

6. The process according to claim 1, wherein the sulphuric acid is added at a temperature ranging from 35° C. to 60° C.

7. The process according to claim 1, wherein the sulphuric acid is added at a temperature of 43±2° C.

8. The process according to claim 1, wherein the Compound (A) is isolated by filtration.

9. The process according to claim 8, wherein prior to isolation by filtration, Compound (A) precipitates and the precipitated solid is mixed with a water immiscible solvent.

10. The process according to claim 9, wherein the solid is mixed with ethyl acetate.

11. The process according to claim 1, wherein Compound (A) isolated in step iii has 0.2% by weight of total impurities or less.

12. The process according to claim 11, wherein Compound (A) has 0.1% by weight of total impurities or less.

13. The process according to claim 11, wherein Compound (A) is devoid of mesityl oxide impurity:

Mesityl oxide.

14. The process according to claim 11 further comprising combining Compound (A), together with one or more pharmaceutically acceptable excipients to produce a pharmaceutical composition.

15. The process according to claim 14, wherein the Compound (A) is present in the pharmaceutical composition in combination with another active pharmaceutical ingredient.

16. The process according to claim 9 wherein after filtration the solid is washed with ethyl acetate.

17. The process according to claim 16, wherein after washing the solid is dried under vacuum at 27±2° C. for 2 hours.

18. The process according to claim 17, wherein after drying the solid is powdered and dried again under vacuum at 53±2° C. for 4 hours.

* * * * *